United States Patent [19]

Grohe et al.

[11] Patent Number: 4,980,353

[45] Date of Patent: Dec. 25, 1990

[54] 1-ARYL-4-QUINOLONE-3-CARBOXYLIC ACIDS

[75] Inventors: Klaus Grohe, Odenthal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 862,863

[22] Filed: May 13, 1986

[30] Foreign Application Priority Data

May 15, 1985 [DE] Fed. Rep. of Germany ....... 3517535

[51] Int. Cl.⁵ .................. A61K 31/495; C07D 401/04
[52] U.S. Cl. .................................... 514/254; 514/187; 514/312; 544/225; 544/363; 546/8; 546/156
[58] Field of Search ...... 544/363, 225, 58.6, 544/128, 286, 287; 514/254, 312, 187; 546/8, 156

[56] References Cited

U.S. PATENT DOCUMENTS

| | | | |
|---|---|---|---|
| 3,966,743 | 6/1976 | Berger et al. | 546/156 |
| 4,533,663 | 8/1985 | Chu | 514/223 |
| 4,623,650 | 11/1986 | Gilligan et al. | 546/156 |
| 4,636,506 | 1/1987 | Gilligan et al. | 546/156 |
| 4,730,000 | 3/1988 | Chu | 544/363 |
| 4,755,513 | 7/1988 | Tone et al. | 544/363 |
| 4,774,246 | 9/1988 | Chu | 544/363 |

FOREIGN PATENT DOCUMENTS

| | | |
|---|---|---|
| 0131839 | 1/1985 | European Pat. Off. . |
| 0154780 | 9/1985 | European Pat. Off. . |
| 3106013 | 9/1982 | Fed. Rep. of Germany . |

OTHER PUBLICATIONS

Chemical Abstracts, vol. 85, No. 11–Sep. 13, 1976, p. 524.
Chu, "Chemical Abstracts," vol. 104, 1986, Col. 104:148892d.

*Primary Examiner*—Richard L. Raymond
*Assistant Examiner*—James H. Turnipseed
*Attorney, Agent, or Firm*—Sprung Horn Kramer & Woods

[57] ABSTRACT

Antibacterially active and animal growth promoting novel 1-aryl-4-quinolone-3-carboxylic acids of the formula

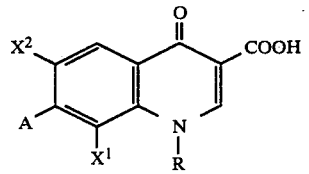

in which
 X is halogen or nitro,
 $X^2$ is halogen,
 R is optionally substituted phenyl, and
 A is halogen or optionally substituted piperazine or pyrrolidine, or pharmaceutically useable hydrates, acid additions salts, alkali metal, alkaline earth metal, silver or guanidinium salts thereof, and/or esters thereof.

9 Claims, No Drawings

1-ARYL-4-QUINOLONE-3-CARBOXYLIC ACIDS

The invention relates to new 1-aryl-4-quinolone-3-carboxylic acids, processes for their preparation and antibacterial agents and feed additives containing these compounds.

It has been found that the new 1-aryl-4-quinolone-3-carboxylic acids of the formula (I)

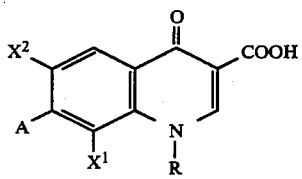

in which
X$^1$ represents halogen or nitro,
X$^2$ represents halogen, in particular fluorine,
R denotes a phenyl radical which is optionally mono- or polysubstituted by halogen atoms, alkyl with 1–4 carbon atoms, alkoxy, alkylmercapto or alkylsulphonyl with in each case up to 3 carbon atoms, nitro, cyano, carboxyl, methylenedioxy or an amine radical

wherein
R$^5$ and R$^6$ can be identical or different and denote hydrogen or alkyl with 1–3 carbon atoms, or denotes an aromatic heterocyclic radical with 5–7 atoms, it being possible for the heteroatom to be S, O or N, and
A represents

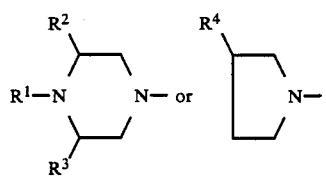

or halogen, in particular chlorine or fluorine,
wherein
R$^1$ represents hydrogen, a branched or straight-chain alkyl group with 1 to 4 carbon atoms, which can optionally be substituted by a hydroxyl or methoxy group, a phenacyl radical which is optionally substituted by hydroxyl, methoxy, chlorine or fluorine, an oxoalkyl radical with 2 to 4 carbon atoms, 4-aminobenzyl, formyl or acetyl, or represents the radical

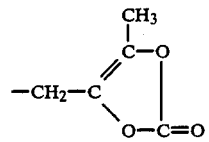

R$^2$ represents hydrogen, methyl or phenyl or thienyl which is optionally substituted by chlorine, fluorine, methyl, hydroxyl or methoxy, R$^3$ represents hydrogen or methyl and R$^4$ represents hydrogen, hydroxyl, amino, alkyl- or dialkylamino with 1 or 2 carbon atoms in the alkyl group, hydroxymethyl, aminomethyl or alkyl- or dialkylaminomethyl with 1 or 2 carbon atoms in the alkyl group,
and pharmaceutically usable hydrates, acid addition salts and alkali metal, alkaline earth metal, silver and guanidinium salts thereof, and in the form of their esters and in other customary prodrug forms, have a powerful antibacterial action.

They are therefore suitable as active compounds for human and veterinary medicine, veterinary medicine also including the treatment of fish for therapy or prevention of bacterial infections.

Preferred compounds of the formula (I) are those in which
X$^1$ represents chlorine, fluorine or nitro,
X$^2$ represents chlorine or fluorine,
R represents a phenyl radical which is optionally substituted by halogen, alkyl, alkoxy, alkylmercapto or alkylsulphonyl with in each case up to 2 carbon atoms in the alkyl part, nitro or cyano, or a pyridine, thiophene, furan or thiazole radical and
A represents

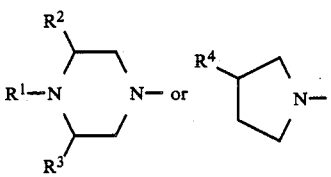

or halogen, in particular chlorine or fluorine,
wherein
R$^1$ represents hydrogen, a branched or straight-chain alkyl group with 1 to 3 carbon atoms, which can optionally be substituted by a hydroxyl group, a phenacyl radical which is optionally substituted by chlorine or fluorine, an oxoalkyl radical with 3 or 4 carbon atoms, 4-aminobenzyl, formyl or acetyl,
R$^2$ represents hydrogen, methyl or phenyl which is optionally substituted by chlorine or fluorine,
R$^3$ represents hydrogen or methyl and
R$^4$ represents hydrogen, hydroxyl, amino, methylamino, ethylamino, aminomethyl, methylaminomethyl, ethylaminomethyl or diethylaminomethyl.

Particularly preferred compounds of the formula (I) are those in which
X$^1$ represents chlorine or fluorine,
X$^2$ represents fluorine,
R represents a phenyl radical which is optionally substituted by chlorine or fluorine, methyl, methoxy, methylmercapto, nitro or cyano and
A represents

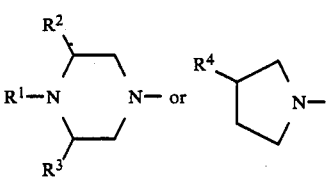

or halogen, in particular chlorine or fluorine, wherein

R¹ represents hydrogen, methyl, ethyl, 2-hydroxyethyl, phenacyl, 2-oxopropyl, 3-oxobutyl or formyl, R² represents hydrogen, methyl or phenyl, R³ represents hydrogen or methyl and R⁴ represents hydrogen, amino, methylamino, aminomethyl, ethylaminomethyl or diethylaminomethyl.

The compounds of the formula (I) in the form of their methyl, ethyl, pivaloyloxymethyl, pivaloyloxyethyl or (5-methyl-2-oxo-1,3-dioxol-4-yl-methyl) esters are furthermore preferred.

It has furthermore been found that the compounds of the formula (I) are obtained by a process in which the 7-halogeno-4-quinolone-3-carboxylic acids of the formula (II)

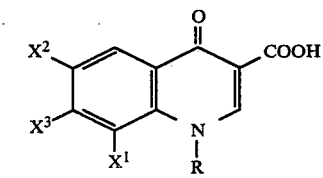

in which

R, X¹ and X² have the abovementioned meaning and X³ represents halogen, preferably chlorine or fluorine, are reacted with amines of the formula (III)

A—H    (III)

in which

A has the abovementioned meaning, if appropriate in the presence of acid-binding agents (method A).

Compounds of the formula (I) according to the invention can also be obtained by a process in which 1,4-dihydro-4-oxo-7-(1-piperazinyl)-quinoline-3-carboxylic acids of the formula (IV)

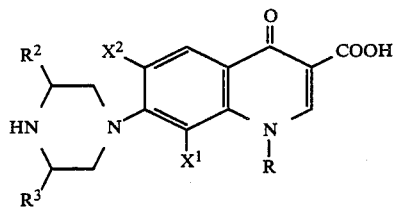

in which

X¹, X², R, R² and R³ have the abovementioned meaning, are reacted with compounds of the formula (V)

R¹—Z    (V)

in which

R¹ has the abovementioned meaning, but cannot be hydrogen, and

Z denotes halogen, in particular chlorine, bromine or iodine, acyloxy, ethoxy or hydroxyl, if appropriate in the presence of acid-binding agents (method B).

Compounds of the formula (I) according to the invention (R¹=CH₃—CO—CH₂CH₂—) are also obtained by a process in which a compound of the formula (IV) is reacted with methyl vinyl ketone of the formula (VI)

CH₃—CO—CH=CH₂    (VI)

(method C).

If 1-methylpiperazine and 6,7,8-trifluoro-1,4-dihydro-4-oxo-1-(4-fluorophenyl)-quinoline-3-carboxylic acid are used as starting substances in the reaction according to method A, the course of the reaction can be represented by the following equation:

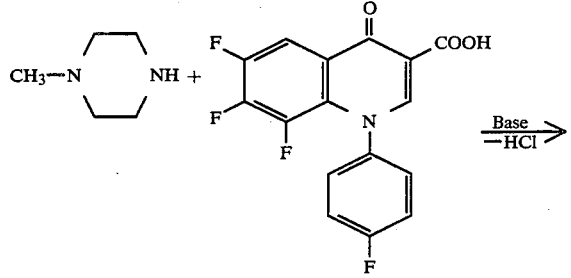

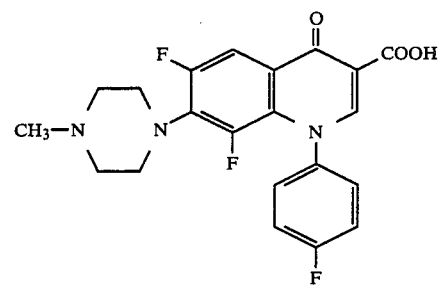

If, for example, chloroacetone and 6,8-difluoro-1,4-dihydro-4-oxo-1-(4-fluorophenyl)-7-(1-piperazinyl)-quinoline-3-carboxylic acid are used as starting substances in the reaction according to method B, the course of the reaction can be represented by the following equation:

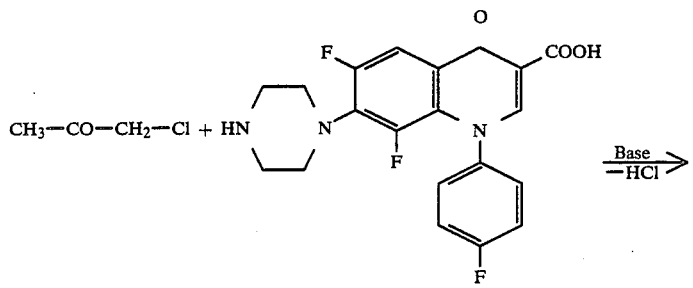

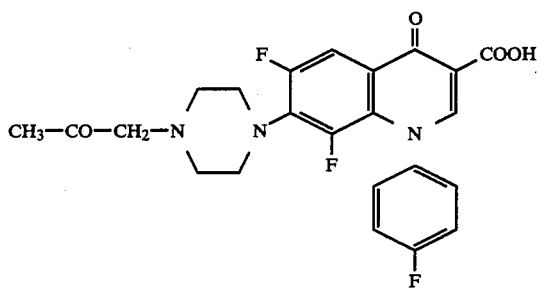

If, for example, methyl vinyl ketone and 6,8-difluoro-1,4-dihydro-4-oxo-1-(4-fluorophenyl)-7-(1-piperazinyl)-quinoline-3-carboxylic acid are used as starting compounds according to method C, the course of the reaction can be represented by the following equation:

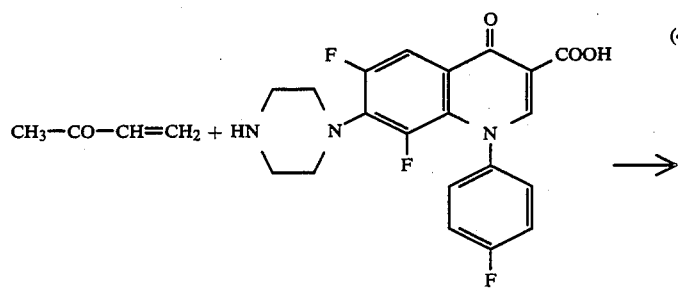

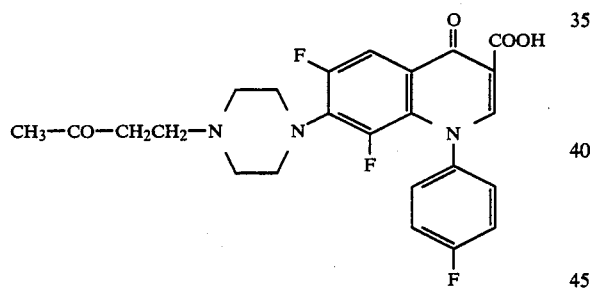

The 7-halogeno-4-quinolone-3-carboxylic acids of the formula (II) used as starting substances according to method A can be prepared in accordance with the following equation:

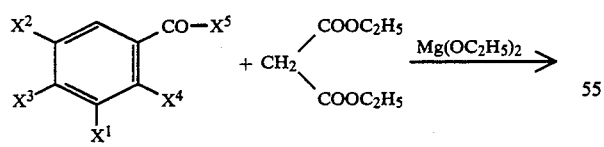

(1), $X^4$, $X^5$ = Cl, Br or F    (2)

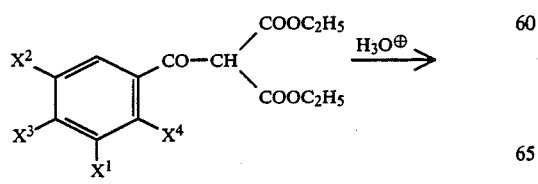

(3)

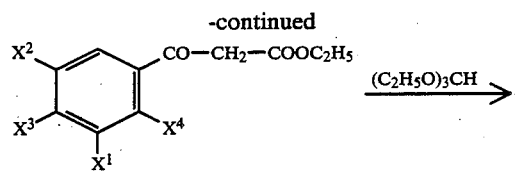

(4)

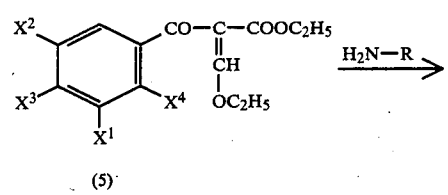

(5)

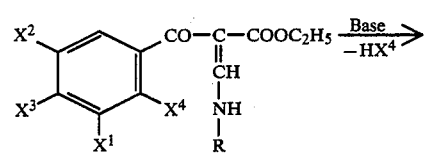

(6)

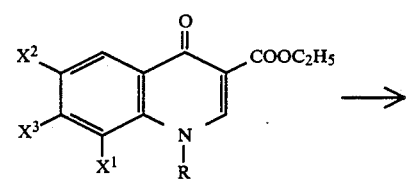

(7)

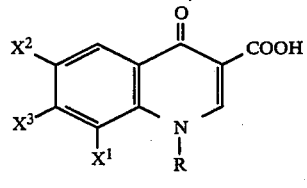

(II)

According to this reaction, diethyl malonate (2) is acylated in the presence of magnesium ethylate with the corresponding benzoyl halide (1) to give the acyl malonate (3) (Organicum, 3rd edition 1964, page 438).

Partial hydrolysis and decarboxylation of (3) in an aqueous medium with catalytic amounts of sulphuric acid or 4-toluenesulphonic acid gives a good yield of the ethyl acylacetate (4), which is converted into the ethyl 2-benzoyl-3-ethoxyacrylate (5) with triethyl orthoformate/acetic anhydride. The reaction of (5) with the amines R—NH$_2$ in a solvent, such as, for example, methylene chloride, an alcohol, chloroform, cyclohexane or toluene gives the desired intermediate products (6) in a slightly exothermic reaction.

The cyclization reaction (6)→(7) is carried out in a temperature range from about 60° to 300° C., preferably 80° to 180° C.

Diluents which can be used are dioxane, dimethylsulphoxide, N-methylpyrrolidone, sulpholane, hexamethylphosphoric acid trisamide and, preferably, N,N-dimethylformamide.

Possible acid-binding agents for this reaction stage are potassium tert.-butanolate, butyl-lithium, lithium-phenyl, phenyl-magnesium bromide, sodium methylate, sodium hydride or sodium or potassium carbonate. Potassium fluoride or sodium fluoride are particularly preferred if hydrogen fluoride has to be split off.

It may be advantageous to employ an excess of 10 mol % of base.

The ester hydrolysis of (7) which takes place in the last step under basic or acid conditions leads to the 4-quinolone-3-carboxylic acids (II).

The 2,3,4,5-tetrafluorobenzoyl chloride used as the starting substance for this synthesis route is already known. 3,5-Dichloro-2,4-difluoro-benzoyl fluoride (boiling point 97°/20 mbar; n$_D^{20}$=1,5148) and 5-chloro-2,3,4-trifluoro-benzoyl fluoride (boiling point 66°-70°/20 mbar; n$_D^{20}$=1.4764) are obtained side by side when tetrachlorobenzoyl chloride is heated at elevated temperatures with potassium fluoride in sulpholane:

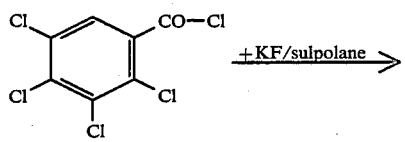

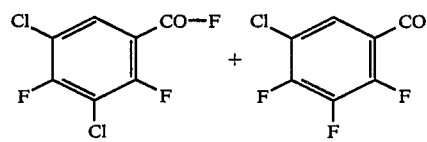

Chlorination of 2,4,5-trifluorobenzoic acid in chlorosulphonic acid leads to 3-chloro-2,4,5-trifluorobenzoic acid, which is reacted as the crude product with thionyl chloride to give 3-chloro-2,4,5-trifluorobenzoyl chloride (boiling point 94°/18 mbar; n$_D^{20}$=1.5164):

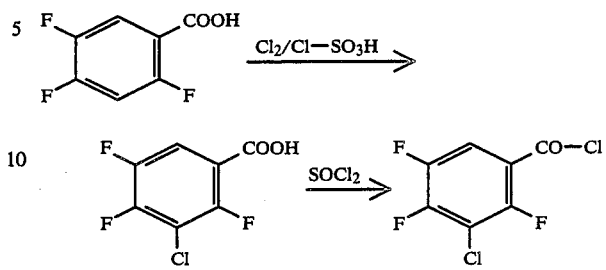

2,4-Dichloro-5-fluoro-3-nitro-benzoyl chloride is obtained by nitration of 2,4-dichloro-5-fluoro-benzoic acid, which is known, to give 2,4-dichloro-5-fluoro-3-nitrobenzoic acid and reaction thereof with thionyl chloride.

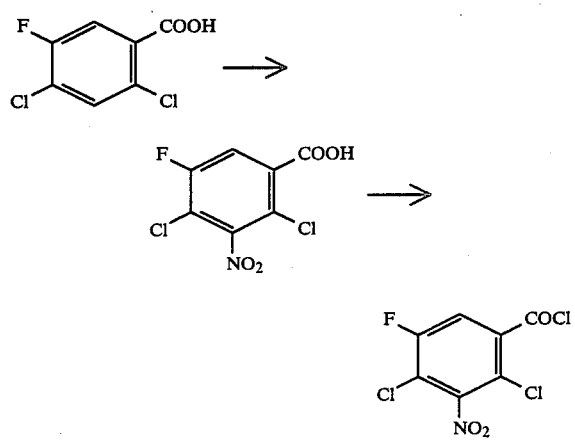

The amines of the formula (III) used as starting substances are known [U.S. Pat. No. 4,166,180 and J. Med. Chem. 26, 1116 (1983)]. Examples which may be mentioned are: piperazine, N-methylpiperazine, N-ethylpiperazine, N-(2-hydroxyethyl)-piperazine, N-(2-methoxyethyl)-piperazine, N-propylpiperazine, N-isopropylpiperazine, N-butylpiperazine, N-(sec.-butyl)-piperazine, N-formylpiperazine, 2-methylpiperazine, cis- and trans-2,6-dimethylpiperazine, 2-phenylpiperazine, 2-(4-fluorophenyl)-piperazine, 2-(4-chlorophenyl)-piperazine, 2-(4-methylphenyl)-piperazine, 2-(4-methoxyphenyl)-piperazine, 2-(4-hydroxyphenyl)-piperazine, 2-(2-thienyl)-piperazine, pyrrolidine, 3-aminopyrrolidine, 3-methylamino-pyrrolidine, 3-aminomethylpyrrolidine, 3-methylaminomethyl-pyrrolidine, 3-dimethylaminomethyl-pyrrolidine, 3-ethylaminomethyl-pyrrolidine and 3-hydroxy-pyrrolidine.

The compounds of the formula (V) used as starting substances are known. Examples which may be mentioned are: methyl iodide, methyl bromide, ethyl iodide, ethyl bromide, 2-hydroxyethyl chloride, 3-hydroxypropyl chloride, n-propyl bromide, isopropyl iodide, n-butyl bromide, sec.-butyl iodide, isobutyl bromide, formic acid/acetic acid anhydride, ethyl formate, formic acid, acetic anhydride and acetyl chloride.

The reaction of (II) with (III) according to method A is preferably carried out in a diluent, such as dimethylsulphoxide, N,N-dimethylformamide, hexamethylphosphoric acid triamide, sulpholane, water, an alcohol, such as methanol, ethanol, n-propanol or isopropanol, glycol monomethyl ether or pyridine. Mixtures of these diluents can also be used.

All the customary inorganic and organic acid-binding agents can be used as the acid-binding agents. These include, preferably, the alkali metal hydroxides, alkali metal carbonates, organic amines and amidines. Acid-binding agents which may be mentioned specifically as being particularly suitable are: triethylamine, 1,4-diazabicyclo-[2,2,2]-octane (DABCO), 1,8-diazabicyclo[5,4,0]-undec-7-ene (DBU) or excess amine (III).

The reaction temperatures can be varied within a substantial range. The reaction is in general carried out between about 20° and 200° C., preferably between 80° and 180° C.

The reaction can be carried out under normal pressure, but also under increased pressure. The reaction is in general carried out under pressures between about 1 and about 100 bar, preferably between 1 and 10 bar.

In carrying out the process according to the invention, 1 to 15 moles, preferably 1 to 6 moles, of the amine (III) are employed per mole of the carboxylic acid (II).

Free amino groups can be protected during the reaction by a suitable amino-protective group, for example the t-butoxycarbonyl, ethoxycarbonyl or acetyl group, and can be removed again when the reaction has ended. An aromatic amino group is introduced via reduction of a nitro group.

The reaction of (IV) with (V) is preferably carried out in a diluent, such as dimethylsulphoxide, dioxane, N,N-dimethylformamide, hexamethyl-phosphoric acid tris-amide, sulpholane, water, an alcohol, such as methanol, ethanol, n-propanol or isopropanol, glycol monomethyl ether or pyridine. Mixtures of these diluents can also be used.

All the customary inorganic and organic acid-binding agents can be used as the acid-binding agents. These include, preferably, the alkali metal hydroxides, alkali metal carbonates, organic amines and amidines. Acid-binding agents which may be mentioned specifically as being particularly suitable are: triethylamine, 1,4-diazabicyclo-[2,2,2]-octane (DABCO) or 1,8-diazabicyclo-[5,4,0]-undec-7-ene (DBU).

The reaction temperatures can be varied within a substantial range. The reaction is in general carried out between about 20° and about 180° C., preferably between 40° and 110° C.

The reaction can be carried out under normal pressure, but also under increased pressure. The reaction is in general carried out under pressures between about 1 and about 100 bar, preferably between 1 and 10 bar.

In carrying out the process according to the invention by method B, 1 to 4 moles, preferably 1 to 1.5 moles, of the compound (V) are employed per mole of the compound (IV).

The reaction of (IV) with (VI) (method C) is preferably carried out in a diluent, such as dioxane, dimethylsulphoxide, N,N-dimethylformamide, methanol, ethanol, isopropanol, n-propanol or glycol monomethyl ether or in mixtures of these diluents.

The reaction temperatures can be varied within a substantial range. The reaction is in general carried out between about 20° C. and about 150° C., preferably between 50° C. and 100° C.

The reaction can be carried out under normal pressure, but also under increased pressure. The reaction is in general carried out under pressures between about 1 and about 100 bar, preferably between 1 and 10 bar.

In carrying out the process according to the invention by method C, 1 to 5 moles, preferably 1 to 2 moles, of the compound (VI) are employed per mole of the compound (IV).

The acid addition salts of the compounds according to the invention are prepared in the customary manner, for example by dissolving the betaine in excess aqueous acid or precipitating the salt with a water-miscible organic solvent (methanol, ethanol, acetone or acetonitrile). It is also possible to heat equivalent amounts of betaine and acid in water until a solution is obtained and then to evaporate this to dryness. Pharmaceutically usable salts are to be understood, for example, as the salts of hydrochloric acid, sulphuric acid, acetic acid, glycolic acid, lactic acid, succinic acid, citric acid, tartaric acid, methanesulphonic acid, galacturonic acid, gluconic acid, glutamic acid or asparaginic acid.

The alkali metal or alkaline earth metal salts are obtained, for example, by dissolving the betaine in less than the stoichiometric amount of alkali metal or alkaline earth metal hydroxide solution, filtering off the undissolved betaine and evaporating the filtrate to dryness. Sodium, potassium or calcium salts are pharmaceutically suitable. By reacting an alkali metal or alkaline earth metal salt with a suitable silver salt, such as silver nitrate, the corresponding silver salts of the 1,4-dihydro-4-oxo-quinoline-3-carboxylic acids are obtained.

New active compounds which may be mentioned specifically, in addition to the compounds listed in the examples, are: 6,8-difluoro-1,4-dihydro-4-oxo-1-(4-fluorophenyl)-7-(3,5-dimethyl-1-piperazinyl)-quinoline-3-carboxylic acid, 6,8-difluoro-1,4-dihydro-4-oxo-1-(3-fluorophenyl)-7-(3,5-dimethyl-1-piperazinyl)-quinoline-3-carboxylic acid, 6,8-difluoro-1,4-dihydro-4-oxo-1-(2-fluorophenyl)-7-(3,5-dimethyl-1-piperazinyl)-quinoline-3-carboxylic acid, 6,8-difluoro-1,4-dihydro-4-oxo-1-(2,4-difluorophenyl)-7-(1-piperazinyl)-quinoline-3-carboxylic acid, 6,8-difluoro-1,4-dihydro-4-oxo-1-(2,4-difluorophenyl)-7-(4-methyl-1-piperazinyl)-quinoline-3-carboxylic acid, 6,8-difluoro-1,4-dihydro-4-oxo-(2,4-difluorophenyl)-7-(3-methyl-1-piperazinyl)-quinoline-3-carboxylic acid, 6,8-difluoro-1,4-dihydro-4-quinoline-3-carboxylic oxo-1-(2,4-difluorophenyl)-7-pyrrolidinyl-quinoline-3-carboxylic acid, 6,8-difluoro-1,4-dihydro-4-oxo-1-(2,4-difluorophenyl)-7-(3-amino-1-pyrrolidinyl)-quinoline-3carboxylic acid, 6,8-difluoro-1,4-dihydro-4-oxo-1-(2,4-di-fluoro-phenyl)-7-(3-methylamino-1-pyrrolidinyl)-quinoline-3-carboxylic acid, 6,8-difluoro-1,4-dihydro-4-oxo-1-(2,4-difluorophenyl)-7-(3-ethylamino-1-pyrrolidinyl)-quinoline-3-carboxylic acid, 6,8-difluoro-1,4-dihydro-4-oxo-1-(2,4-difluorophenyl)-7-(3-dimethylamino-1-pyrrolidinyl)-quinoline-3-carboxylic acid, 6,8-difluoro-1,4-dihydro-4-oxo-1-(2,4-difluorophenyl)-7-(3-ethylamino-methyl-1-pyrrolidinyl)-quinoline-3-carboxylic acid, 8-chloro-6-fluoro-1,4-dihydro-4-oxo-1-phenyl-7-(1-piperazinyl)-quinoline-3-carboxylic acid, 8-chloro-6-fluoro-1,4-dihydro-4-oxo-1-phenyl-7-(4-methyl-1-piperazinyl)-quinoline-3-carboxylic acid, 8-chloro-6-fluoro-1,4-dihydro-4-oxo-1-phenyl-7-(3-methyl-1-piperazinyl)-quinoline-3-carboxylic acid, 8-chloro-6-fluoro-1,4-dihydro-4-oxo-1-phenyl-7-pyrrolidinyl-quinoline-3-carboxylic acid, 8-chloro-6-fluoro-1,4-dihydro-4-oxo-1-phenyl-7-(3-methylamino-1-pyrrolidinyl)-quinoline-3-carboxylic acid, 8-chloro-6-fluoro-1,4-dihydro-4-oxo-1-phenyl-7-(3- ethylaminomethyl-1-pyrrolidinyl)-quinoline-3-carboxylic acid and 6-fluoro-1,4-dihydro-8-nitro-4-oxo-1-phenyl-7-(4-ethyl-1-piperazinyl)-quinoline-3-carboxylic acid.

The invention also relates to compounds of the formula (VII)

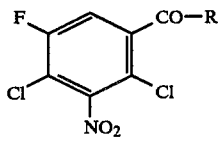

(VII)

in which

R denotes hydroxyl, halogen, in particular chlorine, or alkoxycarbonylmethyl with 1–4 carbon atoms in the alkoxy part.

Example of a tablet according to the invention

| Each tablet contains: | |
|---|---|
| Compound of Example 1 | 583.0 mg |
| Microcrystalline cellulose | 55.0 mg |
| Corn starch | 72.0 mg |
| Insoluble poly-(1-vinyl-2-pyrrolidone) | 30.0 mg |
| Highly disperse silicon dioxide | 5.0 mg |
| Magnesium stearate | 5.0 mg |
| | 750.0 mg |
| The lacquer coating contains: | |
| Poly-(0-hydroxypropyl-0-methyl)-cellulose 15 cp | 6.0 mg |
| Macrogol 4000 recommended INN polyethylene glycols (DAB) | 2.0 mg |
| Titanium(IV) oxide | 2.0 mg |
| | 10.0 mg |

The compounds according to the invention show a broad antibacterial spectrum against Gram-positive and Gram-negative germs, in particular against Enterobacteriaceae above all also against those which are resistant towards various antibiotics, such as, for example, penicillins, cephalosporins, aminoglycosides, sulphonamides and tetracyclines, coupled with a low toxicity.

These useful properties enable them to be used as chemotherapeutic active compounds in medicine and as substances for preserving inorganic and organic materials, in particular all types of organic materials, for example polymers, lubricants, paints, fibers, leather, paper and wood, foodstuffs and water.

The compounds according to the invention are active against a very broad spectrum of microorganisms. It is possible for Gram-negative and Gram-positive bacteria and bacteria-like microorganisms to be combated and the diseases caused by these pathogens to be prevented, alleviated and/or cured with the aid of these compounds.

The compounds according to the invention are particularly active against bacteria and bacteria-like microorganisms. They are therefore particularly suitable in human and veterinary medicine for the prophylaxis and chemotherapy of local and systemic infections caused by these pathogens.

For example, local and/or systemic diseases caused by the following pathogens or by mixtures of the following pathogens can be treated and/or prevented: Micrococcaceae, such as Staphylococci, for example *Staph. aureus* and *Staph. epidermidis* (Staph.=Staphylococcus); Lactobacteriaceae, such as Streptococci, for example *Streptococcus pyogenes*, α and β-haemolyzing Streptococci and non-γ-haemolysing Streptococci, Enterococci and Diplococcus pneumoniae (Pneumococcic), Enterobacteriaceae, such as Eschericiae bacteria of the Eschericia group, for example *Escherichia coli*, Enterobacter bacteria, for example *E. aerogenes* and *E. cloacae* (E.=Enterobacter), Klebsiella bacteria, for example *K. pneumoniae* (K.=Klebsiella), Serratia, for example *Serratia marcescens*, Proteae bacteria of the Proteus group Proteus, for example *Pr. vulgaris*, *Pr. morganii*, *Pr. rettgeri* and *Pr. mirabilis* (Pr.=Proteus); Pseudomonadaceae, such as Pseudomonas bacteria, for example *Ps. aeruginosa* (Ps.=Pseudomonas); Bacteroidaceae, such as Bacteroides bacteria, for example *Bacteroides fragilis*; Mycoplasma, for example *Mycoplasma pneumonia*, and also mycobacteria, for example *Mycobacterium tuberculosis*, *Mycobacterium leprae* and atypical mycobacteria.

The above list of pathogens is given purely by way of example and is in no way to be regarded as limiting. Examples which may be mentioned of diseases which can be prevented, alleviated and/or cured by the compounds according to the invention are: otitis; pharyngitis; pneumonia; peritonitis; pyelonephritis; cystitis; endocarditis; systemic infections: bronchitis; arthritis; local infections; and septic diseases.

The present invention includes pharmaceutical formulations which contain, in addition to non-toxic, inert pharmaceutically suitable excipients, one or more compounds according to the invention or which consist of one or more active compounds according to the invention, and to processes for the preparation of these formulations.

The present invention also relates to pharmaceutical formulations in dosage units. This means that the formulation are in the form of individual parts, for example tablets, dragees, capsules, pills, suppositories and ampules, the active compound content of which correspond to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, one-half, one-third or one quarter of a daily dose.

Non-toxic, inert pharmaceutically suitable excipients are to be understood as meaning solid, semi-solid or liquid diluents, fillers and formulation auxiliaries of all types.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds in addition to the customary excipients, such as (a) fillers and extenders, for example starches, lactose, sucrose, glucose, mannitol and silicic acid, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol or glycerol monostearate, (h) adsorbents, for example kaolin and bentonite, and (i) lubricants, for example talc, calcium stearate, magnesium stearate and solid polyethylene glycols, or mixtures of the substances listed under (a) to (i).

The tablets, dragees, capsules, pills and granules can be provided with the customary coatings and casings, if appropriate containing opacifying agents, and can also be of such composition that they release the active compound or compounds only or preferentially in a particular part of the intestinal tract, if appropriate in a delayed manner, examples of embedding compositions which can be used being polymeric substances and waxes.

The active compound or compounds, if appropriate with one or more of the abovementioned excipients, can also be in a microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silicic acid, talc and zinc oxide, or mixtures of these substances.

Powders and sprays can contain, in addition to the active compound or compounds, the customary excipients, for example lactose, talc, silicic acid, aluminum hydroxide, calcium silicate and polyamide powder, or mixtures of these substances. Sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, maize germ oil, olive oil, castor oil and sesame oil, glycerol, glycerolformal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol and propylene glycol, suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also contain other pharmaceutical active compounds, in addition to the compounds according to the invention.

The abovementioned pharmaceutical formulations are prepared in the customary manner by known methods, for example by mixing the active compound or compounds with the excipient or excipients.

The active compounds or the pharmaceutical formulations can be administered locally, orally, parenterally, intraperitoneally and/or rectally, preferably orally or parenterally, such as intravenously or intramuscularly.

In general, it has proved advantageous both in human medicine and in veterinary medicine to administer the active compound or compounds according to the invention in total amounts of about 0.5 to about 500, preferably 5 to 100 mg/kg of body weight every 24 hours, if appropriate in the form of several individual doses, to achieve the desired results. An individual dose preferably contains the active compound or compounds according to the invention in amounts of about 1 to about 250, in particular 3 to 60 mg/kg of body weight. However, it may be necessary to deviate from the dosages mentioned, and in particular to do so as a function of the species and body weight of the subject to be treated, the nature and severity of the disease, the nature of the formulation and of the administration of the medicament and the period or interval within which administration takes place.

Thus it can in some cases suffice to manage with less than the abovementioned amount of active compound, while in other cases the abovementioned amount of active compound must be exceeded. The particular optimum dosage and mode of administration of the active compounds required can easily be determined by any expert on the basis of his expert knowledge.

The new compounds can be administered in the customary concentrations and formulations together with the feed or with feed formulations or with the drinking water. Infection by Gram-negative or Gram-positive bacteria can thereby be prevented, alleviated and/or cured, and a promotion in growth and an improvement in the feed utilization can therefore be achieved.

The MIC values of some of the compounds according to the invention are given in the following table.

TABLE

| Strain | Minimum inhibitory concentration mcg/ml[(x)] | | | |
| --- | --- | --- | --- | --- |
| | Example No. 2 | Example No. 3 | Example No. 1 | Norfloxacin |
| E. coli 4418 | 0.125 | 0.06 | 0.25 | 0.125 |
| E. coli Neum. | ∫0.015 | ∫0.015 | 0.125 | 0.125 |
| E. coli 455/7 | 8 | 8 | 16 | 8 |
| Klebsiella pneum. 63 | 0.125 | 0.06 | 0.25 | 0.25 |
| Klebsiella pneum. 8085 | 0.06 | ∫0.015 | 0.125 | 0.25 |
| Klebsiella spec. 6179 | 0.25 | 0.06 | 0.5 | 2 |
| Proteus vulg. 1017 | 0.25 | 0.03 | 0.5 | 0.06 |
| Staphylococcus aur. 133 | 0.5 | 0.25 | 0.5 | 1 |

TABLE-continued

| Strain | Minimum inhibitory concentration mcg/ml[x] | | | |
| --- | --- | --- | --- | --- |
| | Example No. 2 | Example No. 3 | Example No. 1 | Norfloxacin |
| *Staphylococcus aur.* 1756 | 0.5 | 0.25 | 0.5 | 1 |
| *Streptococcus faecalis* 27101 | 4.0 | 4.0 | 4.0 | 1 |
| *Pseudomonas aerug.* W. | 4.0 | 1 | 8 | 2 |

[x]Agar dilution test/Denley Multipoint inoculator Isosensitest medium

The following examples illustrate the invention:
Preparation of the starting compounds

EXAMPLE A

7-Chloro-6-fluoro-1,4-dihydro-4-oxo-8-nitro-1-phenyl-quinoline-3-carboxylic acid (A) 2,4-Dichloro-5-fluoro-3-nitro-benzoic acid

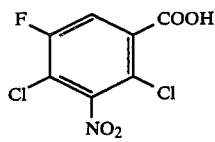

40 ml of concentrated nitric acid are added dropwise to 34 ml of concentrated sulphuric acid, while cooling with ice and stirring. 20.9 g of 2,4-dichloro-5-fluorobenzoic acid are introduced in portions into this nitration mixture, whereupon the temperature rises to 45°–50° C. The mixture is then heated at 90°–100° C. for a further 3 hours, cooled to room temperature and poured onto 350 ml of ice-water and the precipitate is filtered off with suction and washed with water. The moist crude product was dissolved hot in 30 ml of methanol and 150 ml of H₂O were added to the solution.

The precipitate is filtered off with suction in the cold, washed with CH₃OH/H₂O and dried at 80° C. in vacuo. 21.2 g of crude 2,4-dichloro-5-fluoro-3-nitro-benzoic acid are obtained. It is sufficiently pure for further reactions. A sample recrystallized from toluene/petroleum ether gives crystals of melting point 192° C.

(b) 2,4-Dichloro-5-fluoro-3-nitro-benzoyl chloride

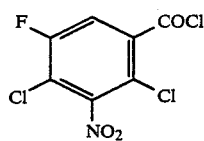

106.6 g of 2,4-dichloro-5-fluoro-3-nitro-benzoic acid are heated at the boiling point under reflux with 250 ml of thionyl chloride for 2 hours. The excess thionyl chloride is then distilled off under normal pressure and the residue is fractionated under a fine vacuum. 104.7 g of 2,4-dichloro-5-fluoro-3-nitro-benzoyl chloride pass over at 110°–115° C./0.08–0.09 mbar. On standing, crystals of melting point 35°–37° C. form.

(c) Ethyl (2,4-dichloro-5-fluoro-3-nitro-benzoyl)-acetate

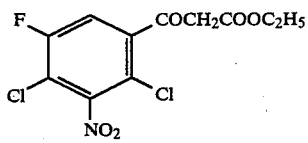

2.1 g of carbon tetrachloride are added to 10.1 g of magnesium filings in 21 ml of ethanol and, when the evolution of hydrogen has started, a mixture of 66.6 g of diethyl malonate, 40 ml of ethanol and 150 ml of toluene is added dropwise at 50°–60° C. The mixture is subsequently stirred at this temperature for 1 hour and cooled to −5° to −10° C. and a solution of 109.2 g of 2,4-dichloro-5-fluoro-3-nitro-benzoyl chloride in 50 ml of toluene is slowly added dropwise. The mixture is then stirred at 0° C. for 1 hour, brought to room temperature overnight and warmed at 40°–50° C. for a further 2 hours. A mixture of 160 ml of water and 10.4 ml of concentrated sulphuric acid is added to the reaction mixture, while cooling with ice, and the organic phase is separated off. The aqueous phase is extracted with toluene, the combined organic extract is washed with saturated sodium chloride solution and dried with sodium sulphate and the solvent is stripped off. 144.5 g of diethyl (2,4-dichloro-5-fluoro-3-nitro-benzoyl)-malonate are obtained as a crude product. After adding 200 ml of water and 0.6 g of 4-toluenesulphonic acid, this is heated under reflux for 3 hours, the mixture is extracted with methylene chloride, the extract is dried with sodium sulphate and the solvent is distilled off in vacuo. 118 g of substituted benzoylacetate are obtained as a crude product. It has a sufficient purity for further reactions.

(d) 7-Chloro-6-fluoro-1,4-dihydro-4-oxo-8-nitro-1-phenyl-quinoline-3-carboxylic acid

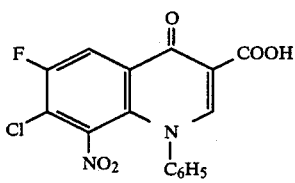

244.8 g of ethyl (2,4-dichloro-5-fluoro-3-nitrobenzoyl)-acetate are heated at 150°–160° C. with 166 g of triethyl orthoformate and 185 g of acetic anhydride for 3 hours. The mixture is concentrated in vacuo and 270 g of ethyl 2-(2,4-dichloro-5-fluoro-3-nitro-benzoyl)-3-ethoxyacrylate are obtained as an oily residue.

9.5 g of aniline are added dropwise to 38 g of this intermediate stage in 100 ml of ethanol, while cooling with ice, and the mixture is stirred at 20° C. for 1 hour. The product which has precipitated is filtered off with suction, after addition of 100 ml of water, and washed with ethanol/H$_2$O (1:1) and dried. 37.9 g of ethyl 2-(2,4-dichloro-5-fluoro-3-nitro-benzoyl)-3-anilino-acrylate (6) (R=C$_6$H$_5$, X$^1$=NO$_2$, X$^2$=F, X$^3$=X$^4$=Cl) of melting point 133°–135° C. are obtained.

13.3 g of DBU are added to 37 g of the abovementioned compound in 100 ml of anhydrous dioxane and the mixture is heated at 100° C. for 4 hours. The solvent is distilled off in vacuo, the residue is taken up in methylene chloride/water, the methylene chloride phase is separated off and dried with sodium sulphate and the methylene chloride is distilled off. 32 g of ethyl 7-chloro-6-fluoro-1,4-dihydro-4-oxo-8-nitro-1-phenyl-quinoline-3carboxylate are obtained as a crude product. After recrystallization from ethanol, the light brown crystals have a melting point of 186°–188° C.

10.5 g of this ester are heated at 150° C. in a mixture of 100 ml of acetic acid, 70 ml of water and 10 ml of concentrated sulphuric acid for 2 hours. The suspension is poured into 300 ml of ice-water and the precipitate is filtered off with suction, washed with water and methanol and dried in vacuo.

Yield: 7.5 g of 7-chloro-6-fluoro-1,4-dihydro-4-oxo-8-nitro-1-phenyl-quinoline-3-carboxylic acid of melting point 249°–250° C.

EXAMPLE B 6,7,8-Trifluoro-1,4-dihydro-4-oxo-1-(4-fluorophenyl)-quinoline-3-carboxylic acid

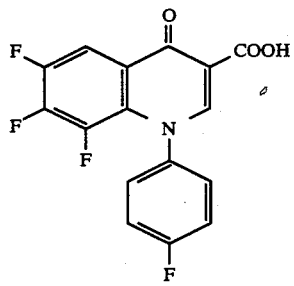

(a) 5.7 g of 4-fluoroaniline are added dropwise to a solution of 16 g of ethyl 3-ethoxy-2-(2,3,4,5-tetrafluorobenzoyl)-acrylate (5) (X$^1$—X$^4$=F) (Appln. Ser. No, 756,469, filed July 18, 1985, now Pat. No. 4,952,695) in 50 ml of ethanol, while cooling with ice and stirring. The mixture is stirred at room temperature for 1 hour, 50 ml of ice-water are added and the precipitate is filtered off cold with suction, rinsed with water and dried at 50° C. over calcium chloride in vacuo. 16.5 g of (6) (R=4-fluorophenyl, X$^1$—X$^4$=F) of melting point 93°–95° C. are obtained.

(b) 2.7 g of sodium fluoride are added to a solution of 16 g of ethyl 2-(2,3,4,5-tetrafluorobenzoyl)-3-(4-fluoroanilino)-acrylate (6) (R=4-fluorophenyl, X$^1$—X$^4$=F) in 60 ml of anhydrous dimethylformamide. The reaction mixture is then stirred under reflux for 2 hours and poured hot onto ice. The precipitate is filtered off with suction, washed with water and dried at 100° C. in vacuo over calcium chloride. After recrystallization from ethanol, 14.8 g of (7) (R=4-fluorophenyl, X$^1$—X$^3$=F) of melting point 228°–229° C. are obtained.

A mixture of 13.6 g of (7) (R=4-fluorophenyl, X$^1$—X$^3$=F), 100 ml of glacial acetic acid, 75 ml of water and 10 ml of concentrated sulphuric acid is heated at the reflux temperature for 2 hours. It is then poured hot onto ice and the precipitate is filtered off with suction, rinsed thoroughly with water and dried in vacuo at 100° C. 11.7 g of 6,7,8-trifluoro-1,4-dihydro-4-oxo-1-(4-fluorophenyl)-quinoline-3-carboxylic acid (II) (R=4-fluorophenyl, X$^1$—X$^3$=F) of melting point 261°–263° C. are obtained. After recrystallization from acetonitrile, the crystals have a melting point of 263°–264° C.

EXAMPLE C 6,7,8-Trifluoro-1,4-dihydro-4-oxo-1-phenyl-quinoline-3-carboxylic acid

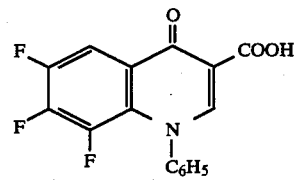

(a) Analogously to Example B (a), using aniline instead of 4-fluoroaniline, the enamino ester (6) (R=C$_6$H$_5$, X$^1$—X$^4$=F) is obtained in 85% yield. Melting point: 88°–90° C.

(b) Cyclization of (6) (R=C$_6$H$_5$, X$^1$—X$^4$=F) analogously to Example B (b) leads to ethyl 6,7,8-trifluoro-1,4-dihydro-4-oxo-1-phenyl-quinoline-3-carboxylate (7) (R=C$_6$H$_5$, X$^1$—X$^3$=F) of melting point 190°–192° C. Yield: 90%.

Acid hydrolysis of (7) (R=C$_6$H$_5$, X$^1$-X$^3$=F) gives 6,7,8-trifluoro-1,4-dihydro-4-oxo-1-phenyl-quinoline-3-carboxylic acid (II) (R=C$_6$H$_5$, X$^1$-X$^3$=F) of melting point 272°–274° C.

Yield: 90%.

EXAMPLE D 6,7,8-Trifluoro-1,4-dihydro-4-oxo-1-(4-chloro-phenyl)-quinoline-3-carboxylic acid

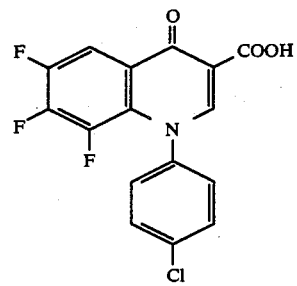

(a) Analogously to Example B (a), using 4-chloroaniline instead of 4-fluoroaniline, the corresponding enamino ester (6) (R=4—Cl—C$_6$H$_4$—, X$^1$—X$^4$=F) is obtained in 75% yield. Melting point: 117°–118° C.

(b) Analogously to Example B (b), ethyl 6,7,8-trifluoro-1,4-dihydro-4-oxo-1-(4-chlorophenyl)-quinoline-3-carboxylate (7) (R=4—Cl—C$_6$H$_4$—, X$^1$—X$^3$=F) is obtained in 85% yield from (6) (R=4—Cl—C$_6$H$_4$-, X$^1$—X$^4$=F). Melting point: 214°–216° C.

Acid hydrolysis gives the corresponding quinolone-carboxylic acid (II) (R=4—Cl—C₆H₄—, X¹—X³=F) in 90% yield. Melting point: 290°-292° C.

EXAMPLE E 6,7,8-Trifluoro-1,4-dihydro-4-oxo-1-(4-methyl-phenyl)-quinoline-3-carboxylic acid

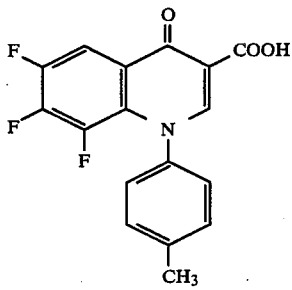

(a) Analogously to Example B (a), using 4-methylaniline instead of 4-fluoroaniline, the corresponding enamino ester (6) (R=4—CH₃—C₆H₄—, X¹—X⁴=F) is prepared in 82% yield. Melting point 110°-111° C.

(b) Analogously to Example B (b), the corresponding quinolonecarboxylic acid ethyl ester (7) (R=4—CH₃—C₆H₄—, X¹—X³=F) is obtained in 90% yield from (6) (R=4—CH₃—C₆H₄—, X¹—X⁴=F).

Melting point: 223°-224° C.

Acid hydrolysis gives the corresponding quinolonecarboxylic acid (II) (R=4—CH₃—C₆H₄—, X¹—X³=F) in 78% yield.

Melting point: 282°-285° C.

EXAMPLE F 6,7,8-Trifluoro-1,4-dihydro-4-oxo-1-(3-chloro-4-fluoro-phenyl)-quinoline-3-carboxylic acid

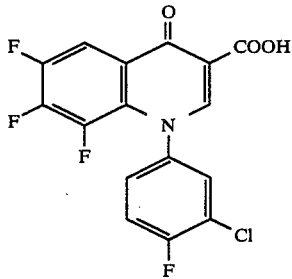

(a) Analogously to Example B (a), using 3-chloro-4-fluoro-aniline instead of 4-fluoro-aniline, the corresponding enamino ester (6) (R=F—C₆H₄—, X¹—X⁴=F) is prepared in 74% yield.

Melting point: 102°-104° C.

(b) Analogously to Example B (b), the corresponding quinolonecarboxylic acid ethyl ester (7) (R=

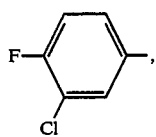

X¹—X³=F) is obtained in 72% yield from (6) (R=F—C₆H₄—, X¹—X⁴=F).

Melting point: 243°-245° C.

Acid hydrolysis gives the corresponding quinolonecarboxylic acid (II) (R=

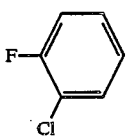

, X¹—X³=F) in 87% yield.

Melting point: 235°-236+ C.

EXAMPLE G 6,7,8-Trifluoro-1,4-dihydro-4-oxo-1-(3,4-difluoro-phenyl)-quinoline-3-carboxylic acid

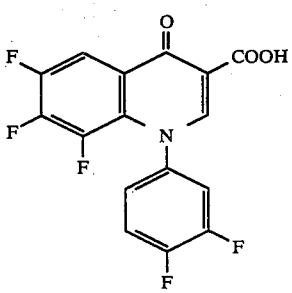

(a) Analogously to Example B (a), using 3,4-difluoroaniline instead of 4-fluoroaniline, the corresponding enamino ester (6) (R=F

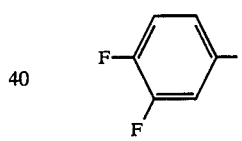

X¹—X⁴=F) is prepared in 70% yield.

Melting point: 87°-90° C.

(b) Analogously to Example B (b), the corresponding quinolonecarboxylic acid ethyl ester (7) (R=

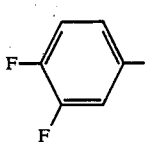

X¹—X³=F) is obtained in 74% yield from (6) (R=

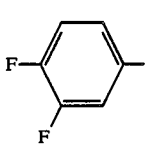

X¹—X⁴=F). Melting point: 236°-238° C.

Acid hydrolysis gives the corresponding quinolonecarboxylic acid (II) (R=

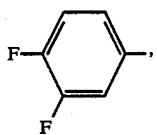

$X^1$—$X^3$=F) in 88% yield. Melting point: 267°–268° C.

EXAMPLE H 6,7,8-Trifluoro-1,4-dihydro-4-oxo-1-(3-pyridyl)-quinoline-3-carboxylic acid

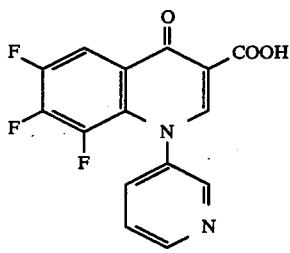

(a) Analogously to Example B (a), using 3-aminopyridine instead of 4-fluoroaniline, the corresponding enamino ester (6) (R=3-pyridyl, $X^1$—$X^4$=F) is prepared in 65% yield. Melting point: 122°–124° C.

(b) Analogously to Example B (b), the corresponding quinolonecarboxylic acid ethyl ester (R=3-pyridyl, $X^1$—$X^4$=F). is obtained in 68% yield from (6) (R=3-pyridyl, $X^1$—$X^4$=F). Melting point: 198°–200° C. Acid hydrolysis gives, after subsequent neutralization, the quinolone-carboxylic acid (II) (R=3-pyridyl, $X^1$—$X^3$=F) in 50% yield.

EXAMPLE I 6,7,8-Trifluoro-1,4-dihydro-4-oxo-1-(3-fluorophenyl)-quinoline-3-carboxylic acid

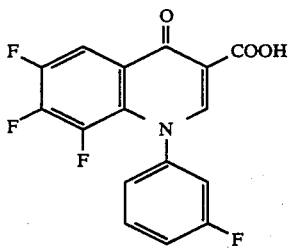

(a) Analogously to Example B (a), using 3-fluoroaniline instead of 4-fluoroaniline, the corresponding enamino ester (6) (R=3-fluorophenyl, $X^1$—$X^4$=F) is prepared in 88% yield.

Melting point: 89°–91° C.

(b) Analogously to Example B (b), the corresponding quinolone-carboxylic acid ethyl ester (7) (R=3-fluorophenyl, $X^1$—$X^3$=F) is obtained in 80% yield from (6) R=3-fluorophenyl, $X^1$—$X^4$=F).

Melting point: 214°–216° C.

Acid hydrolysis gives the corresponding quinolone-carboxylic acid (II) (R=3-fluorophenyl, $X^1$—$X^3$=F) in 85% yield.

Melting point: 254°–256° C.

The following 1,4-dihydro-4-oxo-1-aryl-quinoline-3-carboxylic acids (II) ($X^1$—$X^3$=F or $X^1$=Cl, $X^2$=$X^3$=F) can furthermore be prepared analogously:

R=2-fluorophenyl-, 3,5-difluorophenyl-, 2,6-difluorophenyl-, 2,5-difluorophenyl-, 2,4-difluorophenyl-, 2,4,6-trifluorophenyl-, 2,3,4,5,6-pentafluorophenyl-, 2-fluoro-4-methylphenyl-, 4-fluoro-3-methyl-phenyl-, 4-fluoro-2-methyl-phenyl-, 3-chloro-6-fluoro-phenyl-, 4-chloro-2-fluoro-phenyl-, 3-fluoro-2-methyl-phenyl-, 3-fluoro-6-methyl-phenyl-, 3-chloro-4,6-difluoro-phenyl-, 3,5-dichloro-4-fluoro-phenyl-, 4-fluoro-3-nitro-phenyl-, 4-methoxy-phenyl- and 4-methylmercapto-phenyl-.

EXAMPLE 1

6,8-Difluoro-1,4-dihydro-4-oxo-1-(4-fluorophenyl)-7-(4-methyl-1-piperazinyl)-quinoline-3-carboxylic acid

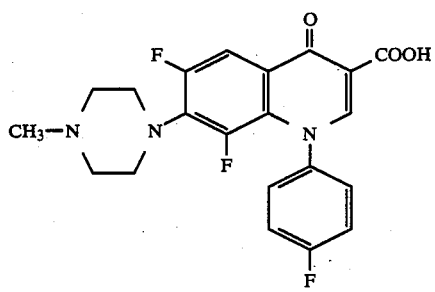

3 g of 6,7,8-trifluoro-1,4-dihydro-4-oxo-1-(4-fluorophenyl)-quinoline-3-carboxylic acid are refluxed in 30 ml of pyridine with 2.7 g of N-methylpiperazine for 6 hours. The solvent is distilled off in vacuo, the residue is taken up in 30 ml of water and the precipitate is filtered off cold with suction, washed with water, dried in vacuo over calcium chloride at 100° C. and recrystallized from glycol monomethyl ether.

Yield: 2.5 g. Melting point: 274°–277° C. (with decomposition).

With concentrated hydrochloric acid, the hydrochloride is obtained analogously to Example 3. Melting point: >300° C. (with decomposition).

EXAMPLE 2

6,8-Difluoro-1,4-dihydro-4-oxo-1-(4-fluorophenyl)-7-(3-methyl-1-piperazinyl)-quinoline-3-carboxylic acid

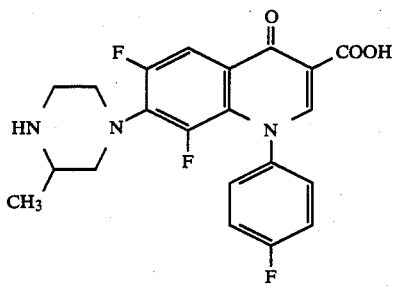

The procedure followed is analogous to Example 1, refluxing being carried out with 2-methylpiperazine for 6 hours and the reaction product being recrystallized from glycol monomethyl ether.

Yield: 2 g, melting point: 260°–262° C. (with decomposition).

EXAMPLE 3

6,8-Difluoro-1,4-dihydro-4-oxo-1-(4-fluorophenyl)-7-(1-piperazinyl)-quinoline-3-carboxylic acid

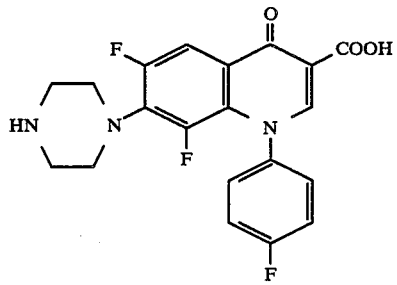

3 g of 6,7,8-trifluoro-1,4-dihydro-4-oxo-1-(4-fluorophenyl)-quinoline-3-carboxylic acid are reacted with 3.1 g of piperazine analogously to Example 1. The reaction product recrystallized from dimethylsulphoxide/ethanol. 1.8 g of melting point 272°-276° C. (with decomposition) is heated at 90°-100° C. with 7.5 ml of water and 7.5 ml of concentrated hydrochloric acid, and 30 ml of ethanol are added to the cooled suspension. The hydrochloride thus formed is filtered off with suction, washed with ethanol and dried.

Yield: 1.4 g, melting point: 333°-335° C. (with decomposition).

EXAMPLE 4

6,8-Difluoro-1,4-dihydro-4-oxo-1-(4-fluorophenyl)-7-(4-ethyl-1-piperazinyl)-quinoline-3-carboxylic acid hydrochloride

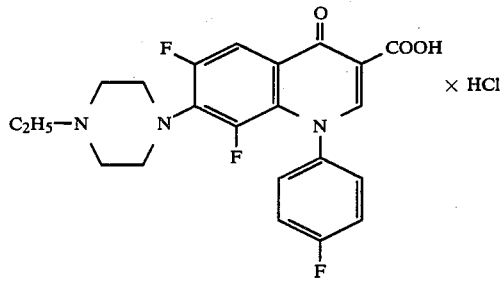

The reaction is carried out analogously to Example 1 with N-ethylpiperazine and the reaction product is then converted into the hydrochloride.

Yield: 2 g, melting point: >300° C. (with decomposition).

EXAMPLE 5

6,8-Difluoro-1,4-dihydro-4-oxo-1-(4-fluorophenyl)-7-(1-pyrrolidinyl)-quinoline-3-carboxylic acid

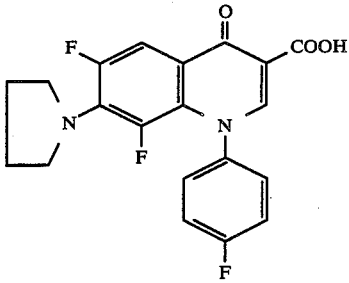

3.37 g of 6,7,8-trifluoro-1,4-dihydro-4-oxo-1-(4-fluorophenyl)-quinoline-3-carboxylic acid are refluxed with 2.3 g of pyrrolidine in 30 ml of absolute pyridine for 6 hours. The solvent is distilled off in vacuo, the residue is suspended in 50 ml of ice-water, the pH is brought to 1-2 with hydrochloric acid and the precipitate is filtered off with suction, washed with water and dried. 2.5 g of (I) (R=4-fluorophenyl, $X^1=X^2=F$, A=

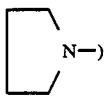

of melting point 282°-284° C. are obtained. Recrystallization from glycol monomethyl ether/ethanol.

EXAMPLE 6

6,8-Difluoro-1,4-dihydro-4-oxo-1-(4-fluorophenyl)-7-(3-amino-1-pyrrolidinyl)-quinoline-3-carboxylic acid

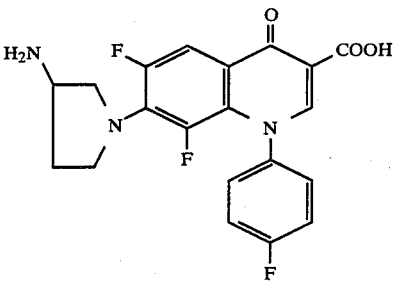

(a) 6 g of 3-acetamido-pyrrolidine are added to a solution of 3.2 g of 6,7,8-trifluoro-1,4-dihydro-4-oxo-1-(4-fluorophenyl)-quinoline-3-carboxylic acid in 30 ml of dimethylsulphoxide. The mixture is heated at 120°-130° C. for 6 hours, the solvent is stripped off in vacuo, the residue is taken up in ice-water, the mixture is brought to pH 1-2 with concentrated hydrochloric acid and the precipitate is filtered off with suction and rinsed thoroughly with water 3.4 g of (I) (R=4-fluorophenyl, $X^1=X^2=F$, A=

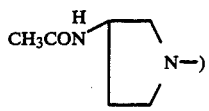

are obtained.

(b) The product-described above is hydrolyzed with hydrochloric acid at 80°-100° C. 2.4 g of 6,8-difluoro-1,4-dihydro-4-oxo-1-(4-fluorophenyl)-7-(3-amino-1-pyrrolidinyl)-quinoline-3-carboxylic acid hydrochloride of melting point >300° C. (with decomposition) are obtained.

EXAMPLE 7

6,8-Difluoro-1,4-dihydro-4-oxo-1-phenyl-7-(4-methyl-1-piperazinyl)-quinoline-3-carboxylic acid

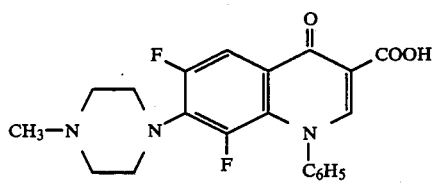

The preparation is carried out analogously to Example 1. 6,7,8-Trifluoro-1,4-dihydro-4-oxo-1-phenylquinoline-3-carboxylic acid and N-methylpiperazine are used as starting substances. 6,8-Difluoro-1,4-dihydro-4-oxo-1-phenyl-7-(4-methyl-1-piperazinyl)-quinoline-3-carboxylic acid hydrochloride of melting point >300° C. (with decomposition) is obtained in a good yield. Melting point of the betaine: 225°-230° C.

EXAMPLE 8

6,8-Difluoro-1,4-dihydro-4-oxo-1-phenyl-7-(1-piperazinyl)-quinoline-3-carboxylic acid

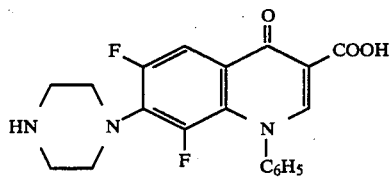

The preparation is carried out analogously to Example 3. 6,7,8-Trifluoro-1,4-dihydro-4-oxo-1-phenylquinoline-3-carboxylic acid and piperazine are used as starting substances. The corresponding quinoline-3-carboxylic acid hydrochloride (I) (R=C$_6$H$_5$, X$^1$=X$^2$=F, A=piperazinyl) of melting point >300° C. is obtained in 75% yield. Melting point of the betaine: 288°-300° C. (with decomposition).

EXAMPLE 9

6,8-Difluoro-1,4-dihydro-4-oxo-1-phenyl-7-(3-methyl-1-piperazinyl)-quinoline-3-carboxylic acid

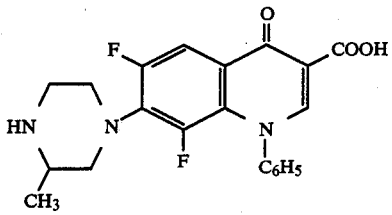

The synthesis is carried out analogously to Example 1. 6,7,8-Trifluoro-1,4-dihydro-4-oxo-1-phenyl-quinoline-3-carboxylic acid and 2-methylpiperazine are used as the starting substances. The corresponding quinoline-3-carboxylic acid hydrochloride (I) (R=C$_6$H$_5$, X$^1$=X$^2$=F, A=3-methyl-1-piperazinyl) of melting point <300° C. is obtained in 70% yield.

EXAMPLE 10

6,8-Difluoro-1,4-dihydro-4-oxo-1-phenyl-7-(4-ethyl-1-piperazinyl)-quinoline-3-carboxylic acid

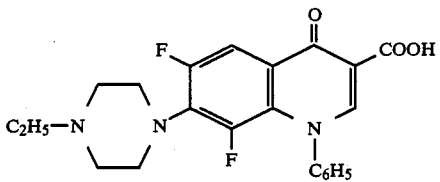

The synthesis is carried out analogously to Example 1. 6,7,8-Trifluoro-1,4-dihydro-4-oxo-1-phenyl-quinoline-3-carboxylic acid and N-ethylpiperazine are used as the starting substances. The corresponding quinoline-3-carboxylic acid hydrochloride (I) (R=C$_6$H$_5$, X$^1$=X$^2$=F, A=4-ethyl-1-piperazinyl) of melting point >300° C. is obtained in 60% yield. Melting point of the betaine: 227°-229° C.

EXAMPLE 11

6,8-Difluoro-1,4-dihydro-4-oxo-1-(4-chlorophenyl)-7-(4-methyl-1-piperazinyl)-quinoline-3-carboxylic acid hydrochloride

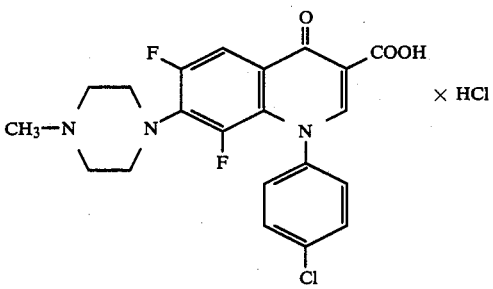

The synthesis is carried out analogously to Example 1. 6,7,8-Trifluoro-1,4-dihydro-4-oxo-1-(4-chlorophenyl)-quinoline-3-carboxylic acid and N-methylpiperazine are used as starting substances. The corresponding quinoline-3-carboxylic acid hydrochloride (I) (R=4—Cl—C$_6$H$_4$—, X$^1$=X$^2$=F, A=4-ethyl-1- piperazinyl) of melting point >300° C. is obtained in 78% yield. Melting point of the betaine: 274°-278° C.

EXAMPLE 12

6-Fluoro-1,4-dihydro-4-oxo-8-nitro-1-phenyl-7-(4-methyl-1-piperazinyl)-quinoline-3-carboxylic acid hydrochloride

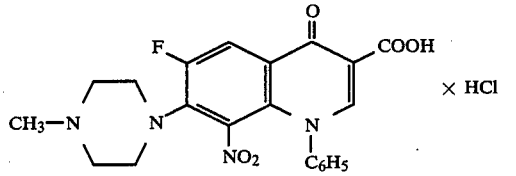

The synthesis is carried out analogously to Example 1 (2 hours reflux). 7-Chloro-6-fluoro-1,4-dihydro-4-oxo-8-nitro-1-phenyl-quinoline-3-carboxylic acid and N-methylpiperazine are used as the starting substances. The quinoline-3-carboxylic acid hydrochloride (I) (R=C$_6$H$_5$, X$^1$=NO$_2$, X$^2$=F, A=4-methyl-1-piperazinyl) obtained as the reaction product has a melting point >300° C. (with decomposition). Melting point of the betaine: 240°-245° C.

EXAMPLE 13

6,8-Difluoro-1,4-dihydro-4-oxo-1-(4-methylphenyl)-7-(1-piperazinyl)-quinoline-3-carboxylic acid hydrochloride

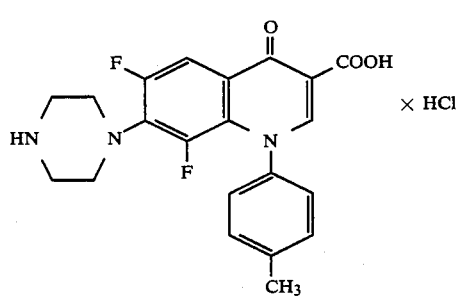

The synthesis is carried out analogously to Example 3. 6,7,8-Trifluoro-1,4-dihydro-4-oxo-1-(4-methylphenyl)-quinoline-3-carboxylic acid and piperazine are used as the starting substances. The quinoline-3-carboxylic acid hydrochloride (I) (R=4-methylphenyl, X$^1$=X$^2$=F, A=piperazinyl) obtained as the reaction product in a good yield has a melting point >300° C.

EXAMPLE 14

6,8-Difluoro-1,4-dihydro-4-oxo-1-(4-methylphenyl)-7-(4-ethyl-1-piperazinyl)-quinoline-3-carboxylic acid hydrochloride

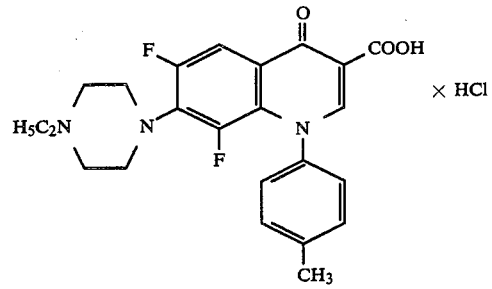

The synthesis is carried out analogously to Example 1. 6,7,8-Trifluoro-1,4-dihydro-4-oxo-1-(4-methylphenyl)-quinoline-3-carboxylic acid and N-ethylpiperazine are used as starting substances. The quinoline-3-carboxylic acid hydrochloride (I) (R=4-methylphenyl, X$^1$=X$^2$=F, A=4-ethyl-1-piperazinyl) obtained as the reaction product in 68% yield has a melting point >300° C. Melting point of the betaine: 198°-200° C.

EXAMPLE 15

6,8-Difluoro-1,4-dihydro-4-oxo-1-(3,4-difluoro-phenyl)-7-(1-pyrrolidinyl)-quinoline-3-carboxylic acid

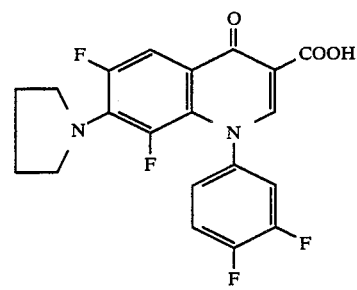

The synthesis is carried out analogously to Example 5. 6,7,8-Trifluoro-1,4-dihydro-4-oxo-1-(3,4-difluorophenyl)-quinoline-3-carboxylic acid and pyrrolidine are used as starting substances. The quinoline-3-carboxylic acid (I) (R=3,4-difluorophenyl, X$^1$=X$^2$=F, A=pyrrolidinyl) obtained as the reaction product has a melting point of 295° C.

EXAMPLE 16

6,8-Difluoro-1,4-dihydro-4-oxo-1-(3,4-difluoro-phenyl)-7-(1-piperazinyl)-quinoline-3-carboxylic acid hydrochloride

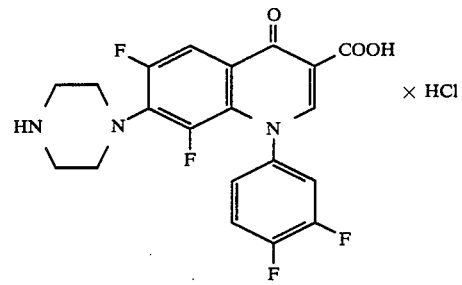

The synthesis is carried out analogously to Example 3. 6,7,8-Trifluoro-1,4-dihydro-4-oxo-1-(3,4-difluorophenyl)-quinoline-3-carboxylic acid and piperazine are used as starting substances. The quinoline-3-carboxylic acid hydrochloride (I) (R=3,4-dichlorophenyl, X¹=X²=F, A=piperazinyl) obtained as the reaction product has a melting point >300° C.

EXAMPLE 17

6,8-Difluoro-1,4-dihydro-4-oxo-1-(3-fluorophenyl)-7-(4-methyl-1-piperazinyl)-quinoline-3-carboxylic acid hydrochloride

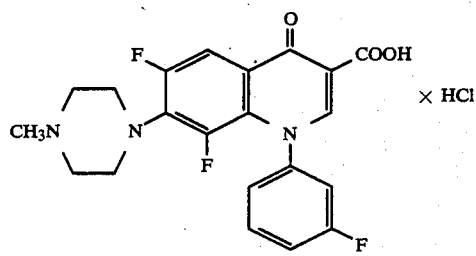

The synthesis is carried out analogously to Example 1. 6,7,8-Trifluoro-1,4-dihydro-4-oxo-1-(3-fluorophenyl)-quinoline-3-carboxylic acid and N-methylpiperazine are used as starting substances. The quinoline-3-carboxylic acid hydrochloride (I) (R=3-fluorophenyl, X¹=X²=F, A=4-methyl-1-piperazinyl) obtained as the reaction product has a melting point >300° C.

The following quinoline-3-carboxylic acids substituted in the 7-position and the corresponding hydrochlorides (I) can be prepared analogously (melting points of the hydrochlorides >300° C.):

| Example | R | X¹ | X² | A |
|---|---|---|---|---|
| 18 | 4-chlorophenyl | F | F | HN⟩N— |
| 19 | 4-chlorophenyl | F | F | ⟩N— (pyrrolidinyl) |
| 20 | 4-methylphenyl | F | F | Et-N⟩N— |
| 21 | 3-chloro-4-fluorophenyl | F | F | HN⟩N— |
| 22 | 3-chloro-4-fluorophenyl | Cl | F | CH₃N⟩N— (betaine m.p. 268° C.) |
| 23 | 3,4-difluorophenyl | F | F | CH₃N⟩N— |
| 24 | 3,4-difluorophenyl | F | F | Et-N⟩N— |
| 25 | 3,4-difluorophenyl | Cl | F | HN⟩N— |
| 26 | 3,4-difluorophenyl | F | F | CH₃N-H⟩N— |
| 27 | 3-fluorophenyl | F | F | HN⟩N— |
| 28 | 3-fluorophenyl | F | F | Et-N-CH₂⟩N— (H) |
| 29 | 3-fluorophenyl | Cl | F | CH₃N⟩N— |
| 30 | 3-pyridyl | F | F | ⟩N— |
| 31 | 3-pyridyl | F | F | CH₃N⟩N— |
| 32 | 2-fluorophenyl | F | F | HN⟩N— |
| 33 | 2-fluorophenyl | F | F | EtN⟩N— |
| 34 | 2-fluorophenyl | F | F | HN⟩N—(CH₃) |
| 35 | 2-fluorophenyl | Cl | F | HN⟩N— |
| 36 | 3,5-difluorophenyl | F | F | CH₃N⟩N— |

-continued

| Example | R | $X^1$ | $X^2$ | A |
|---|---|---|---|---|
| 37 | 2,6-difluorophenyl | F | F | HN⟩N— (piperazinyl) |
| 38 | 4-fluoro-3-methyl-phenyl | F | F | HN⟩N— (piperazinyl) |
| 39 | 4-fluoro-3-methyl-phenyl | F | F | HN⟩N— with CH₃ (methylpiperazinyl) |
| 40 | 4-fluoro-3-methyl-phenyl | F | F | H₅C₂—NH⟩N— |
| 41 | 4-fluoro-3-methyl-phenyl | F | F | CH₃—N(H)—CH₂⟩N— |
| 42 | 4-methoxyphenyl | F | F | CH₃N⟩N— |
| 43 | 4-methoxyphenyl | Cl | F | HN⟩N— |
| 44 | 4-methylmercap-tophenyl | F | F | ⟩N— |
| 45 | 4-methylmercap-tophenyl | F | F | HN⟩N— |

EXAMPLE 46

6,8-Difluoro-1,4-dihydro-4-oxo-1-(4-fluorophenyl)-7-[4-(2-oxo-propyl)-1-piperazinyl]-quinoline-3-carboxylic acid hydrochloride

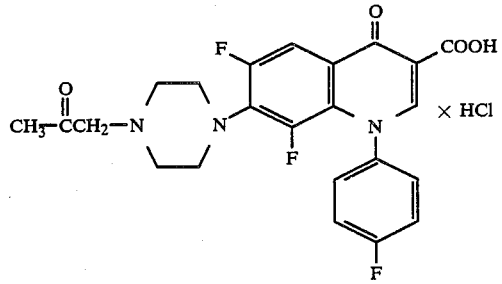

0.7 g of chloroacetone and 1.05 g of triethylamine are added to 2 g of 6,8-difluoro-1,4-dihydro-4-oxo-1-(4-fluorophenyl)-7-(1-piperazinyl)-quinoline-3-carboxylic acid in 25 ml of dimethylformamide and the mixture is heated at 80° C. for 3 hours. The suspension is concentrated in vacuo and the residue is stirred with water, filtered off with suction and dried. The product is heated in 15 ml of dilute hydrochloric acid (1:1), precipitated with 30 ml of ethanol, filtered off with suction and dried.

Yield: 1.9 g, melting point: >300° C. (with decomposition).

EXAMPLE 47

6,8-Difluoro-1,4-dihydro-4-oxo-1-(4-fluorophenyl)-7-[4-(3-oxo-butyl)-1-piperazinyl]-quinoline-3-carboxylic acid hydrochloride

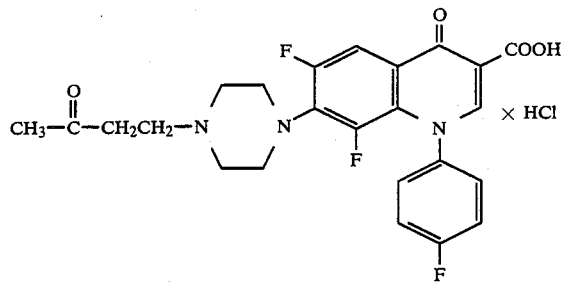

2 g of 6,8-difluoro-1,4-dihydro-4-oxo-1-(4-fluorophenyl)-7-(1-piperazinyl)-quinoline-3-carboxylic acid and 1.95 g of methyl vinyl ketone are heated under reflux in 25 ml of ethanol for 7 hours, the resulting precipitate is filtered off with suction and dissolved in dilute hydrochloric acid (1:1) and the product is precipitated with ethanol.

Yield: 1.6 g, melting point >300° C. (with decomposition).

It will be understood that the specification and examples are illustrative but not limitative of the present invention and that other embodiments within in the spirit and scope of the invention will suggest themselves to those skilled in the art.

What is claimed:

1. A 1-aryl-4-quinoline-3-carboxylic acid of the formula $$\text{(structure: quinolone with } X^2 \text{ at 6-position, A at 7-position, } X^1 \text{ at 8-position, N-R at 1-position, COOH at 3-position, =O at 4-position)}$$

in which
- $X^1$ is chlorine, fluorine or nitro,
- $X^2$ is chlorine or fluorine with the proviso that $X^1$ and $X^2$ are not simultaneously fluorine,
- R is phenyl, or phenyl substituted by at least one of halogen, alkyl with 1 to 4 carbon atoms, alkoxy, alkylmercapto or alkylsulphonyl with in each case up to 3 carbon atoms, nitro, cyano, carboxyl, methylenedioxy, a pyridine, thiophene, furan or thiazole radical, or an amine radical of the formula $$-N\begin{matrix}R^5\\R^6\end{matrix},$$

$R^5$ and $R^6$ each independently is hydrogen, or alkyl with 1 to 3 carbon atoms, A is $$R^1-N\underset{R^3}{\overset{R^2}{\diagdown}}\hspace{-2pt}\diagup N-, \quad \underset{}{\overset{R^4}{\diagdown}}N-$$

or halogen,
- $R^1$ is hydrogen, alkyl with 1 to 4 carbon atoms, alkyl with 1 to 4 carbon atoms and substituted by a hydroxyl or methoxy group, phenacyl, phenacyl substituted by hydroxyl, methoxy, chlorine or fluorine, an oxoalkyl radical with 2 to 4 carbon atoms, 4-aminobenzyl, formyl or acetyl, or the radical $$-CH_2-C\begin{matrix}CH_3\\ \diagup C-O\\ \diagdown O-C=O\end{matrix}$$

- $R^2$ is hydrogen, methyl, phenyl, thienyl, or phenyl or thienyl substituted by chlorine, fluorine, methyl, hydroxyl or methoxy,
- $R^3$ is hydrogen or methyl, and
- $R^4$ is hydrogen, hydroxyl amino, alkyl- or dialkylamino with 1 or 2 carbon atoms in each alkyl group, hydroxymethyl, aminomethyl or alkyl- or dialkylaminomethyl with 1 or 2 carbon atoms in each alkyl group, or a pharmaceutically usable hydrate, acid addition salt, alkali metal, alkaline earth metal, silver or guanidinium salt thereof, and/or an $C_1$–$C_3$-alkyl ester thereof.

2. A 1-aryl-4-quinoline-3-carboxylic acid hydrate, salt and/or ester according to claim 1, in which
- $X^1$ is chlorine, fluorine or nitro,
- $X^2$ is chlorine or fluorine, with the proviso that $X^1$ and $X^2$ are not simultaneously fluorine,
- R is phenyl, phenyl substituted by halogen, alkyl, alkoxy, alkylmercapto or alkylsulphonyl with an each case up to 2 carbon atoms in each alkyl part, nitro or cyano, or is a pyridine, thiophene, furan or thiazole radical, A is $$R^1-N\underset{R^3}{\overset{R^2}{\diagdown}}\hspace{-2pt}\diagup N-, \quad \underset{}{\overset{R^4}{\diagdown}}N-$$

or halogen,
- $R^1$ is hydrogen, alkyl with 1 to 3 carbon atoms, alkyl with 1 to 3 carbon atoms substituted by a hydroxyl group, phenacyl, phenacyl substituted by chlorine or fluorine, an oxoalkyl radical with 3 or 4 carbon atoms, 4-aminobenzyl, formyl or acetyl,
- $R^2$ is hydrogen, methyl, phenyl, phenyl substituted by chlorine or fluorine,
- $R^3$ is hydrogen or methyl, and
- $R^4$ is hydrogen, hydroxyl, amino, methylamino, ethylamino, aminomethyl, methylaminomethyl, ethylaminomethyl or diethylaminomethyl.

3. A 1-aryl-4-quinolone-3-carboxylic acid hydrate, salt and/or ester according to claim 1, in which
- $X^1$ is chlorine,
- $X^2$ is fluorine,
- R is phenyl, or phenyl substituted by chlorine or fluorine, ethyl, methoxy, methylmercapto, nitro or cyano, A is $$R^1-N\underset{R^3}{\overset{R^2}{\diagdown}}\hspace{-2pt}\diagup N-, \quad \underset{}{\overset{R^4}{\diagdown}}N-$$

or halogen,
- $R^1$ is hydrogen, methyl, ethyl, 2-hydorxyethyl, phenacyl, 2-oxopropyl, 3-oxobutyl or formyl,
- $R^2$ is hydrogen, methyl or phenyl,
- $R^3$ is hydrogen or methyl, and
- $R^4$ is hydrogen, amino, methylamino, aminomethyl, ethylaminomethyl or diethylaminomethyl.

4. A 1-aryl-4-quinolone-3-carboxylic acid ester according to claim 1, in the form of the methyl, ethyl, pivaloyloxymethyl, pivaloyl-oxyethyl or (5-methyl-2-oxo-1,3-dioxol-4-yl-methyl) ester.

5. A compound according to claim 1, selected from the group consisting of 6-fluoro-1,4-dihydro-4-oxo-8-nitro-1-phenyl-7-(4-methyl-1-piperazinyl)-quinoline-3-carboxylic and a hydrate, salt and/or ester thereof.

6. A compound according to claim 1, selected from the group consisting of 8-chloro-6-fluoro-1,4-dihydro-4-oxo-1-phenyl-7-(1-piperazinyl)-quinoline-3-carboxylic acid, 8-chloro-6-fluoro-1,4-dihydro-4-oxo-1-phenyl-7-(4-methyl-1-piperazinyl)-quinoline-3-carboxylic acid, 8-chloro-6-fluoro-1,4-dihydro-4-oxo-1-phenyl-7-(3-methyl-1-piperazinyl)-quinoline-3-carboxylic acid, 8- chloro-6-fluoro-1,4-dihydro-4-oxo-1-phenyl-7-pyrrolidinyl-quinoline-3-carboxylic acid, 8-chloro-6-fluoro-b 1,4-dihydro-4-oxo-1-phenyl-7-(3-methylamino-1-pyrrolidinyl)-quinoline-3-carboxylic acid, 8-chloro-6-fluoro-b 1,4-dihydro-4-oxo-1-phenyl-7-(3-methylaminoethylaminomethyl-1-pyrrolidinyl)-quinoline-3-carboxylic acid and 6-fluoro-1,4-dihydro-8-nitro-4-oxo-1-phenyl-7-(4-ethyl-1-piperazinyl)-quinoline-3-carboxylic acid, and a hydrate, salt and/or ester thereof.

7. An antibacterial composition comprising an antibacterially effective amount of an acid, hydrate, salt and/or ester thereof according to claim 1 in the combination with a pharmaceutically acceptable diluent.

8. A unit dose of a composition according to claim 7 in the form of a tablet, capsule or ampule.

9. A composition according to claim 7, wherein the diluent is an animal feed base.

* * * * *

UNITED STATES PATENT AND TRADEMARK OFFICE
CERTIFICATE OF CORRECTION

PATENT NO. : 4,980,353

DATED : December 25, 1990

INVENTOR(S) : Grohe et al.

Page 1 of 2

It is certified that error appears in the above-identified patent and that said Letters Patent is hereby corrected as shown below:

| | |
|---|---|
| Col. 32, claim 1 line 67 | Delete " quinoline " and substitute -- quinolone -- |
| Col. 33, claim 2 line 66 | Delete " quinoline " and substitute -- quinolone -- |
| Col. 34, line 4 | Delete " an " and substitute -- in -- |
| Col. 34, line 29 | Delete " ethylaminomethyl " and substitute -- ethylaminoethyl -- |
| Col. 34, line 48 | Delete " hydorxyethyl " and substitute -- hydroxyethyl -- |
| Col. 34, line 61 | After " carboxylic " insert -- acid -- |
| Col. 35, line 3 | After " fluoro- " delete " b " |

UNITED STATES PATENT AND TRADEMARK OFFICE
CERTIFICATE OF CORRECTION

PATENT NO. : 4,980,353
DATED : December 25, 1990
INVENTOR(S) : Grohe et al

It is certified that error appears in the above-indentified patent and that said Letters Patent is hereby corrected as shown below:

Col. 35, line 5   After "fluoro-" delete "b" and delete "methylamino -"

Signed and Sealed this

Eighth Day of June, 1993

Attest:

MICHAEL K. KIRK

Attesting Officer    Acting Commissioner of Patents and Trademarks